United States Patent [19]

Frey

[11] Patent Number: 4,530,116
[45] Date of Patent: Jul. 23, 1985

[54] ANCHORING SHANK FOR A BONE IMPLANT

[75] Inventor: Otto Frey, Winterthur, Switzerland

[73] Assignee: Sulzer Brothers Limited, Winterthur, Switzerland

[21] Appl. No.: 539,564

[22] Filed: Oct. 6, 1983

[30] Foreign Application Priority Data

Oct. 15, 1982 [CH] Switzerland .................. 6018/82

[51] Int. Cl.³ .......................... A61F 1/04; A61F 5/04
[52] U.S. Cl. ........................................ 623/23; 3/1.91;
128/92 C
[58] Field of Search .................. 3/1.91, 1.912, 1.913,
3/1.911; 128/92 C, 92 CA

[56] References Cited

U.S. PATENT DOCUMENTS 4,199,824  4/1980  Niederer ........................ 3/1.913
4,261,063  4/1981  Blanquaert ..................... 128/92 C
4,404,693  9/1983  Zweymuller ................... 128/92 C

FOREIGN PATENT DOCUMENTS 159035  2/1983  Fed. Rep. of Germany ....... 3/1.912

Primary Examiner—Richard J. Apley
Assistant Examiner—David J. Isabella
Attorney, Agent, or Firm—Kenyon & Kenyon

[57] ABSTRACT

The anchoring shank is provided with a plurality of depressions which are arranged in fish-scale manner. Each depression is of arch-like shape with flanks which taper conically towards the proximal end of the shank. In addition, each depression merges into the shank at the distal end while having a trough parallel to the axis of the shank.

The depressions serve to improve the adhesion between the bone cement bed and the shank obviates looseness caused by shrinkage of the bone cement bed.

11 Claims, 3 Drawing Figures

ANCHORING SHANK FOR A BONE IMPLANT

This invention relates to an anchoring shank for a bone implant.

More particularly, this invention relates to an anchoring shank for a prosthesis.

As is known, various types of endoprostheses have been made for implanting in a bone via a cement bed. It has also been known to provide the surface of such prostheses with means to improve the adhesion between the shank of the prostheses and the surrounding cement bed, for example as described in Swiss Pat. No. 547,631. However, it has been found that, due to the shrinkage of a cement bed in both diameter and volume, shanks with the known surface structures may not always insure an adhesion between the bone cement and the anchoring shank with the necessary safety. In the course of time, this may lead to a relative movement between the shank and the cement bed such that the bed is "ground-up" with the resulting attrition or cement particles moving between the sliding surfaces of the joint.

Accordingly, it is an object of the invention to improve the adhesion between an anchoring shank of a bone implant and a bone cement bed.

It is another object of the invention to insure an adhesion bond between an anchoring shank and a bone cement bed despite shrinkage in the bone cement bed.

Briefly, the invention provides an anchoring shank for a bone implant which has a tapered configuration which narrows along a longitudinal axis from a proximal end to a free distal end and which is provided with a plurality of arch-like depressions in a surface of the shank. These depressions extend essentially in the direction of the longitudinal axis of the shank and each depression has flanks which taper conically from the distal end towards the proximal end.

The arch-like depressions are arranged on at least parts of the shank surface in a fish scale type distribution, i.e. in parallel rows with the depressions of adjacent rows being in offset relation.

The form of the depressions permits a shrinking bone cement to shrink into the depressions and not away from the surface of the shank. Further, the conical pattern of the flanks of the depressions permits a self-strengthening effect when the prosthesis is driven deeper into a bone since this results in a compaction of the bone cement bed. At the same time, the conical form of the depressions facilitates removal of the shank for a re-operation.

Advantageously, the depressions merge into the shank surface at the distal end of each and each depression has a trough which is parallel to the longitudinal axis of the shank. With these two additional features, the penetration of the bone cement into the depressions is facilitated and the cement bed can be retained in a largely undamaged state in the case of a re-operation.

Where the anchoring shank is used for a femur head prosthesis, the shank generally has a length of about 10 to 25 centimeters and a width of from 1 to 4 centimeters. In this case, each depression is made with a height of, for example, about 5 millimeters, a width at the base of the arch of about 3 to 5 millimeters and a depth at the summit of the arch of less than 2 millimeters.

These and other objects and advantages of the invention will become more apparent from the following detailed description taken in conjunction with the accompanying drawings wherein.

Figure 1:
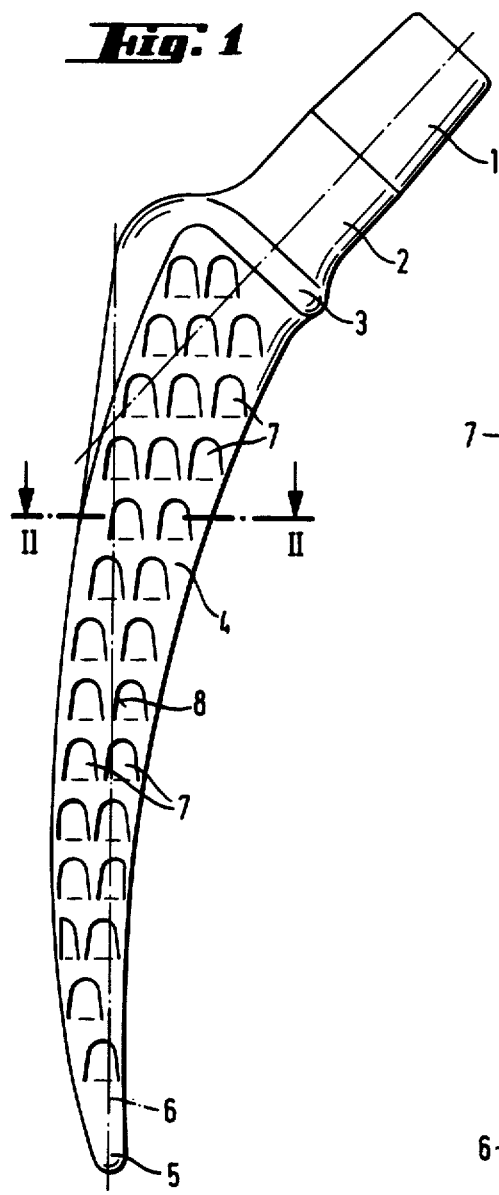
FIG. 1 illustrates a side view of a shank for a femur head prosthesis in accordance with the invention.

Referring to FIG. 1, the femur head prosthesis includes a conical pin 1 at a proximal end, for example for receiving an articular ball (not shown), a neck 2 and a collar 3. In addition, the prosthesis has an anchoring shank 4 of curved form which conically tapers towards a distal end 5 from the collar 3. The shank 4 has a rectangular cross-section as indicated in FIG. 2 and tapers conically on each side to the distal end 5 relative to a longitudinal axis 6.

Figure 3:
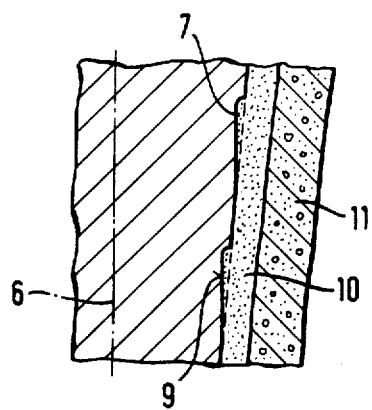
FIG. 3 illustrates a view taken on line III—III of FIG. 2.

Each surface of the shank 4 is provided with a plurality of individual discrete arch-like depressions 7 each of which has a pair of flanks 8 tapering conically in a direction from the distal end 5 and converging to an apex towards the proximal end. In addition, as shown in FIG. 3, each depression 7 merges into the shank surface at a distal end due to the conical form of the shank 4 and has a trough 9 which is aligned parallel to the longitudinal axis 6.

As shown in FIG. 1, the depressions 7 are arranged in a fish-scale manner, i.e. the depressions 7 are disposed in parallel transverse rows with the depressions 7 of the adjacent rows being in offset relation. Further, each depression is about 5 millimeters in height, as viewed, with a width at the base of an arch of about 3 to 5 millimeters and a depth at the summit of less than two millimeters. Each depression 7 forms a trough parallel to the longitudinal axis 6 which gradually merges into the shank surface from a proximal to a distal direction to permit bone cement to penetrate into the individual depressions 7 during insertion within a bone cement bed 10 (see FIG. 2) thereby compacting the cement due to the conical form of the flanks.

Figure 2:
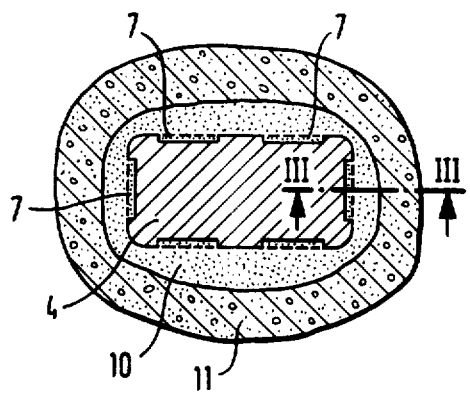
FIG. 2 illustrates a view taken on line II—II of the anchoring shank in a cement bed within a bone.

Referring to FIG. 2, when inserting the shank 4 into the bone cement bed 10 which has been previously filled into a surgically prepared cavity of a femur bone 11, the bone cement penetrates into the individual depressions 7. Because of the conical form of the flanks 8 of each depression, the bone cement becomes somewhat compacted. As the bone cement bed 10 shrinks during and after a polymerization reaction as is known, the bone cement ring contracts somewhat both in a peripheral direction and in diameter. As a result, a good adhesion in the individual depressions 7 is obtained. Thus, the danger of a relative movement occurring between the shank 4 and the bone cement bed 10 is reduced.

The invention thus provides an anchoring shank with a surface which is able to effect a good adhesion between the shank and a bone cement bed but also one which permits the shank to be removed for a re-operation if required. Further, because of the shape of the individual depressions, the bone cement which moves into these depressions becomes somewhat compacted so that subsequent shrinkage does not create a looseness between the shank and the bone cement bed.

What is claimed is:

1. An anchoring shank for a bone implant having a tapered configuration narrowing along a longitudinal axis from a proximal end to a free distal end, at least one surface of said shank having a plurality of transverse parallel rows of individual discrete arch-like depressions therein, each of said depressions extending essentially in the direction of said longitudinal axis, each of said depressions having flanks tapering conically from said distal end and converging to an apex towards said proximal end whereby said depressions form a trough parallel to said longitudinal axis gradually merging into said shank surface from a proximal to a distal direction to permit bone cement to penetrate into said individual depressions during insertion within the cement thereby compacting the cement due to the conical form of said flanks.

2. An anchoring shank as set forth in claim 1 wherein each depression merges into said shank surface at a distal end and has a trough parallel to said axis.

3. A prosthesis comprising
an anchoring shank of curved form conically tapered from a proximal end towards a distal end thereof, said shank having a plurality of surfaces disposed along a longitudinal axis; and
a plurality of transverse rows of individual discrete depressions disposed in each said surface, each said depression having a pair of flanks tapering conically in a direction from said distal end and converging to an apex towards said proximal end whereby said depressions form a trough parallel to said longitudinal axis gradually merging into said shank surface from a proximal to a distal direction to permit bone cement to penetrate into said individual depressions during insertion within the cement thereby compacting the cement due to the conical form of said flanks.

4. A prosthesis as set forth in claim 3 wherein said depressions are disposed in offset relation between adjacent rows.

5. A prosthesis as set forth in claim 4 wherein each depression merges into a respective shank surface at a distal end and has a trough parallel to said axis.

6. A prosthesis as set forth in claim 4 wherein each depression has a height of about 5 millimeters, a width at a base thereof of about 3 to 5 millimeters and a depth of less than 2 millimeters.

7. A prosthesis as set forth in claim 3 wherein said shank has a rectangular cross-section.

8. A prosthesis comprising
a prosthesis neck;
a collar adjacent said neck;
a curved shank extending from said neck to a free distal end along a longitudinal axis, said shank having a plurality of surfaces disposed in tapered relation to said axis; and
a plurality of transverse rows of individual discrete depressions disposed in each said surface, each said depression having a pair of flanks tapering conically in a direction away from said distal end and converging to an apex towards a proximal end of said shank whereby said depressions form a trough parallel to said longitudinal axis gradually merging into said shank surface from a proximal to a distal direction to permit bone cement to penetrate into said individual depressions during insertion within the cement thereby compacting the cement due to the conical form of said flanks.

9. A prosthesis as set forth in claim 8 wherein said depressions are disposed in parallel rows transversely along said axis and in offset relation between adjacent rows.

10. A prosthesis as set forth in claim 8 wherein each depression merges into a respective shank surface at a distal end and has a trough parallel to said axis.

11. A prosthesis as set forth in claim 8 wherein said shank has a rectangular cross-section.

* * * * *

UNITED STATES PATENT AND TRADEMARK OFFICE
CERTIFICATE OF CORRECTION

PATENT NO. : 4,530,116
DATED : July 23, 1985
INVENTOR(S) : Otto Frey

It is certified that error appears in the above-identified patent and that said Letters Patent is hereby corrected as shown below:

In the Abstract, line 10 change "shank obviates" to -shank and obviates-

Signed and Sealed this

Eleventh Day of February 1986

[SEAL]

Attest:

DONALD J. QUIGG

Attesting Officer  Commissioner of Patents and Trademarks